(12) United States Patent
Weiss

(10) Patent No.: US 6,830,547 B2
(45) Date of Patent: Dec. 14, 2004

(54) ATTACHMENT DEVICES FOR SURGICAL INSTRUMENTS

(76) Inventor: Sol Weiss, 17144 Bullock St., Encino, CA (US) 90068

( * ) Notice: Subject to any disclaimer, the term of this patent is extended or adjusted under 35 U.S.C. 154(b) by 104 days.

(21) Appl. No.: 10/095,950

(22) Filed: Mar. 11, 2002

(65) Prior Publication Data

US 2002/0165435 A1 Nov. 7, 2002

Related U.S. Application Data

(63) Continuation-in-part of application No. 09/978,604, filed on Oct. 15, 2001, now Pat. No. 6,394,950.
(60) Provisional application No. 60/241,067, filed on Oct. 17, 2000, and provisional application No. 60/286,188, filed on Apr. 24, 2001.

(51) Int. Cl.[7] ................................................. A61B 1/30
(52) U.S. Cl. ....................................... 600/221; 600/223
(58) Field of Search ................................ 600/188, 221, 600/223, 199, 200, 205, 212, 219, 220, 222, 241, 245; 433/29, 31

(56) References Cited

U.S. PATENT DOCUMENTS

| 220,762 | A | * | 10/1879 | Huffman |
| 559,122 | A | * | 4/1896 | Daily |
| 3,146,776 | A | * | 9/1964 | Duncan |
| 3,153,267 | A | * | 10/1964 | Rowland, Jr. |
| 3,789,835 | A | * | 2/1974 | Whitman |
| 4,067,323 | A | * | 1/1978 | Troutner et al. |
| 4,432,352 | A | * | 2/1984 | Wineland |

* cited by examiner

*Primary Examiner*—Cary E. O'Connor
(74) *Attorney, Agent, or Firm*—Mitchell Silberberg & Knupp LLP

(57) ABSTRACT

A surgical portable light connector having an attachment plate so as to firmly fit onto instruments such as speculums, retractors or other instruments in the field for illumination, holding tenaculums and securing suctioning tubes and other devices. This portable attachment plate connector allows the surgeon or operators to gain the benefit of less obstructed view and conduct their procedures with more adequate space within the field of instrumentation.

29 Claims, 5 Drawing Sheets

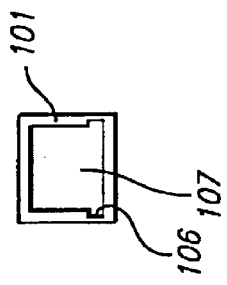
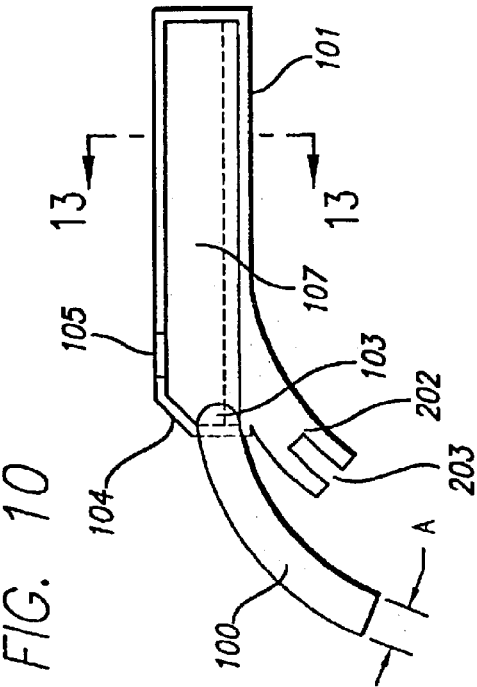
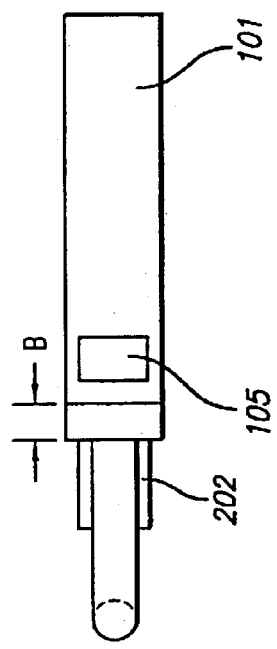
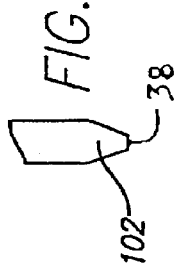
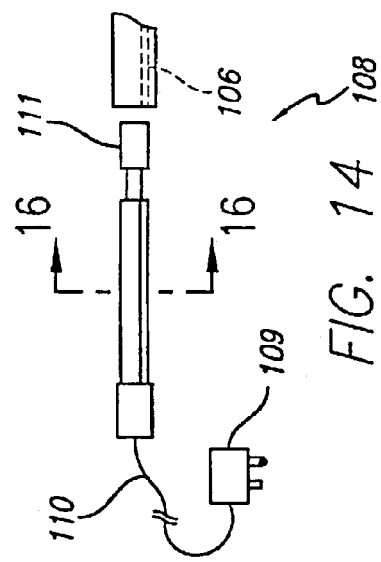
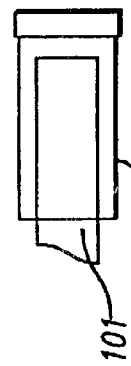
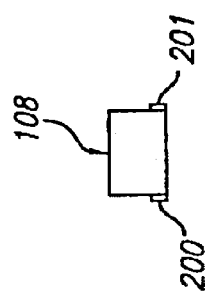

ATTACHMENT DEVICES FOR SURGICAL INSTRUMENTS

CROSS REFERENCE TO RELATED APPLICATIONS

This application is a Continuation-In-Part of application Ser. No. 09/978,604 filed Oct. 15, 2001, now U.S. Pat. No. 6,394,950 issued May 28, 2002, which claims the benefit of Provisional Application No. 60/241,067 filed Oct. 17, 2000 and Provisional Application No. 60/286,188 filed Apr. 24, 2001.

FIELD OF THE INVENTION

The invention relates to portable light cone diagnostic and surgical instruments, and other uses requiring an attachment device to be used in abdominal, thoracic, vaginal and other body procedures.

GENERAL BACKGROUND AND STATE OF THE ART

Certain surgical, diagnostic and other devices are used for examining cavities and surgical openings that may include prior art devices known as speculums, retractors, or other investigative instruments that require an attachable device to allow for holding a light source, additional instrumentations, suctioning equipment and irrigation tubes without obstructing the view of the operator or the surgeon.

In my provisional application Serial No. 60/286,188, entitled Light Cone and filed Apr. 24, 2001, I disclose a light cone for use with a surgical instrument, such as the speculum in my U.S. Pat. No. 5,868,668 and in my pending applications in [0001].

There is thus a need for all surgical instruments, such as speculums, both metal and plastic, to have provisions for a light cone that have an attachable plate which is sized and shaped to conform and attached to the upper blade of the speculums as seen in FIG. 17 and FIG. 18.

In reviewing my earlier patents, I showed how the cone of light served both as transmission of light but also the tight fitting cone of light inserted into a receptacle, 37. Other instruments do not have these ports available, therefore there is a need for attaching the body and the cone of light to the speculum by means of this demonstrated attachment plate mechanism, 202, as shown in FIGS. 10 and 12.

SUMMARY OF THE INVENTION

It is the object of this invention to provide an attachment plate as part and addition to the light cone connector for attachment to a speculum, retractor or other such like diagnostic and surgical equipment for light transmission and/or other equipment.

It is still further an object of this invention to provide a portable light cone for illuminating the surgeon's working area without interfering with the surgeon's view through the instrument, avoids contamination with the surgical procedure and is away from the containment area and away from the the bleeding area and is reusable.

It is another object of this invention to provide such a surgical instrument having a passageway for feeding a suction tube therethrough to suction out blood, smoke or tissue or the like during an invasive procedure without interfering with the surgeon's view through the instrument.

It is the object of this portable connector attachment plate invention to aid in holding other equipment, i.e., tenaculums, without interfering with the operator or surgeon's view through the instrumentation field.

BRIEF DESCRIPTION OF DRAWINGS

FIG. 10 is an elevational view of a light transmitting device adapted to be used with the device of FIGS. 1 and 2.

FIG. 11 is a detailed view showing the tapered distal end of a light-carrying cone;

FIG. 12 is a top plan view of the device of FIG. 10;

FIG. 13 is a view taken along lines 13—13 of FIG. 10;

FIG. 14 is an elevational view of a prior art illuminating device used with the device of FIG. 10;

FIG. 15 is an elevational view of a resilient sleeve adapted to be used with the device of FIG. 10; and FIG. 16 is a view taken along lines 16—16 of FIG. 14

DETAILED DESCRIPTION OF THE PREFERRED EMBODIMENTS

Figures 1, 2:
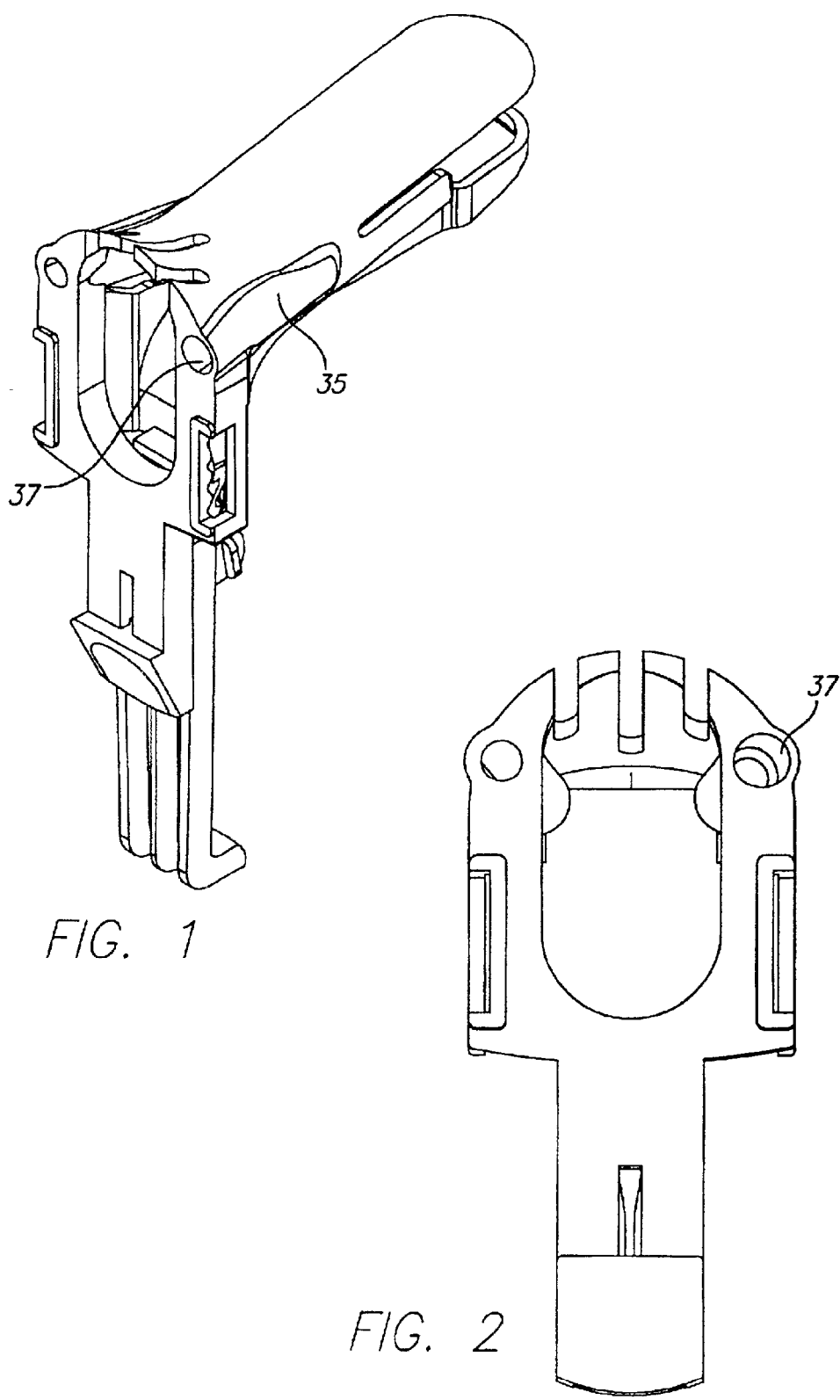
FIG. 1 is an angled view of the speculum (refer to cross reference to related application).
FIG. 2 is a rear view of the speculum (refer to cross reference to related application).

As seen in FIG. 10, a portable light carrying cone 100 is shown having a base or connector body 101, which may be of clear plastic, directing light from an illuminator or other light sources. The cone 100 shown here is solid and has a tapered distal portion 102 (FIG. 11) and a bulblike proximal end 103 (FIG. 10), within the connector body 101. The tapered portion of 102 of the cone 100 is used to fit snugly or tightly into the end 37 (FIG. 1) of cone 35 so that light can be transmitted. The bulb shaped proximal portion 103 (FIG. 10) acts as a magnifier to attract light rays concentrating them into the cone 100 for transmitting the light. The tapered portion 104 of the connector body 101 allows for non-cone absorbing light to be scattered into the area where the cone 100 and body 101 of the connector are directed.

In my patent application Ser. No. 09/978,604 filed Oct. 15, 2001, the attachment relied upon a tapered cone fitting snugly into a tapered receptacle 37 of a speculum. The patent application discloses in addition an attachment process 202 wherein the tapered cut out that may be curved or straight, 203, is attached to the rim of speculums or edge of retractors, other diagnostic or surgical devices and other instrumentations that would allow for the light cone to transmit light to the desired location.

This attachment plate may also lend to holding not only cones of light but other instruments. These adaptations would permit instruments to be attached and held in a position which would not obscure the vision of the surgeon and/or operator. They may be of metal, plastic or combinations thereof.

These portable attachment devices can be metal or plastic. As a plastic device, it can be disposable so as to avoid sterilization procedures. This provides an economic advantage saving time and costs.

FIGS. 10 and 12 show the window opening 105 in body 101 that allows for heat to be dissipated, and the tracks 106 at the bottom of the opening 107 stabilize the illuminator body 111 and center it so that the bulb of the lighting device, to be discussed, doesn't come in contact with the walls of the connector body 101.

FIG. 14 shows a conventional prior art illuminating device 108 having a transformer 109, an electrical cord 110, and a light source 111. Light source 111 is shown inserted into cone 100, the terminal or bulb and extending to bulb end 103 (FIG. 10). Any suitable illuminator may be used. For example, the vaginal illuminator system No. 78103 manufactured and sold by Welch Allyn of Skaneateles Fall, N.Y. may be used. The opening 107 and sidewalls (FIG. 13) of housing 101 accommodate the outer configuration of light source 111.

The angled tapered front portion 104 of the body 101 permits light to be dispersed to different areas that are targeted as well. The body 101 of the connector also has tracks or slots 106 (FIG. 13) to receive flanges 200, 201 on the outer body of the illuminator 111 and its bulb to allow for not stabilizing the light bulb thereof into the center of the cavity 107 of the body 101 so that is does not contact the walls (FIG. 13) of the connector body 101.

The posterior portion of the connector body 101 may have an elastic or rubber adapter 112 (FIG. 15) with a hollow tubular interior so that the end of the body 101 fits therein for attaching to different light illuminating devices which may be of different sizes.

The cone 100 and connector body 101 are portable, and they are not dependent on other devices or handles. They are sacrificed with each procedure, as other equipment requires them to be.

The cone 100 and body 101 may be of a simplified plastic construction that allows for easy manufacturing as a two-part injection mold for plastic applications. This can also be made by metal molding or casting. The tapered tip 102 produces a tight connection with a circular opening, such as opening 37, in any instrument receptacle designed for this procedure.

Body 101 has an open area 105 of the connector body 101 near the cone projection that allows heat to escape caused by the bulb of illuminator 111.

Cone 100 has a curved cone projection 103 that may be solid plastic and provides the transmission of the light from the bulb of illuminator 111 or any other source to a specific area directed by the tip of the cone 100 out through end 38 which my be of clear plastic.

There thus is disclosed in FIGS. 10 to 15 a light connector possessing at its front portion a curved solid plastic cone tapered at its distal end for light transmission. The connector body unites with the cone having a bulb shaped proximal portion that allows for light to be collected and transmitted to the end of the curved cone. This allows light to be carried into difficult areas as well as directed to the front of medical devices through an aperture that permits the tapered cone to fit tightly. The connector body of this unit has a slot opening in the rear portion permitting the light bulb and the illuminator body to penetrate into the cavity of the connector body. The connector body has a tracking mechanism that keeps the illuminator and light bulb in a central position without touching the inner walls of the plastic housing of the connector body. The front portion of the connector body has a window opening that permits the escape of heat from the illuminator bulb.

Figure 17:
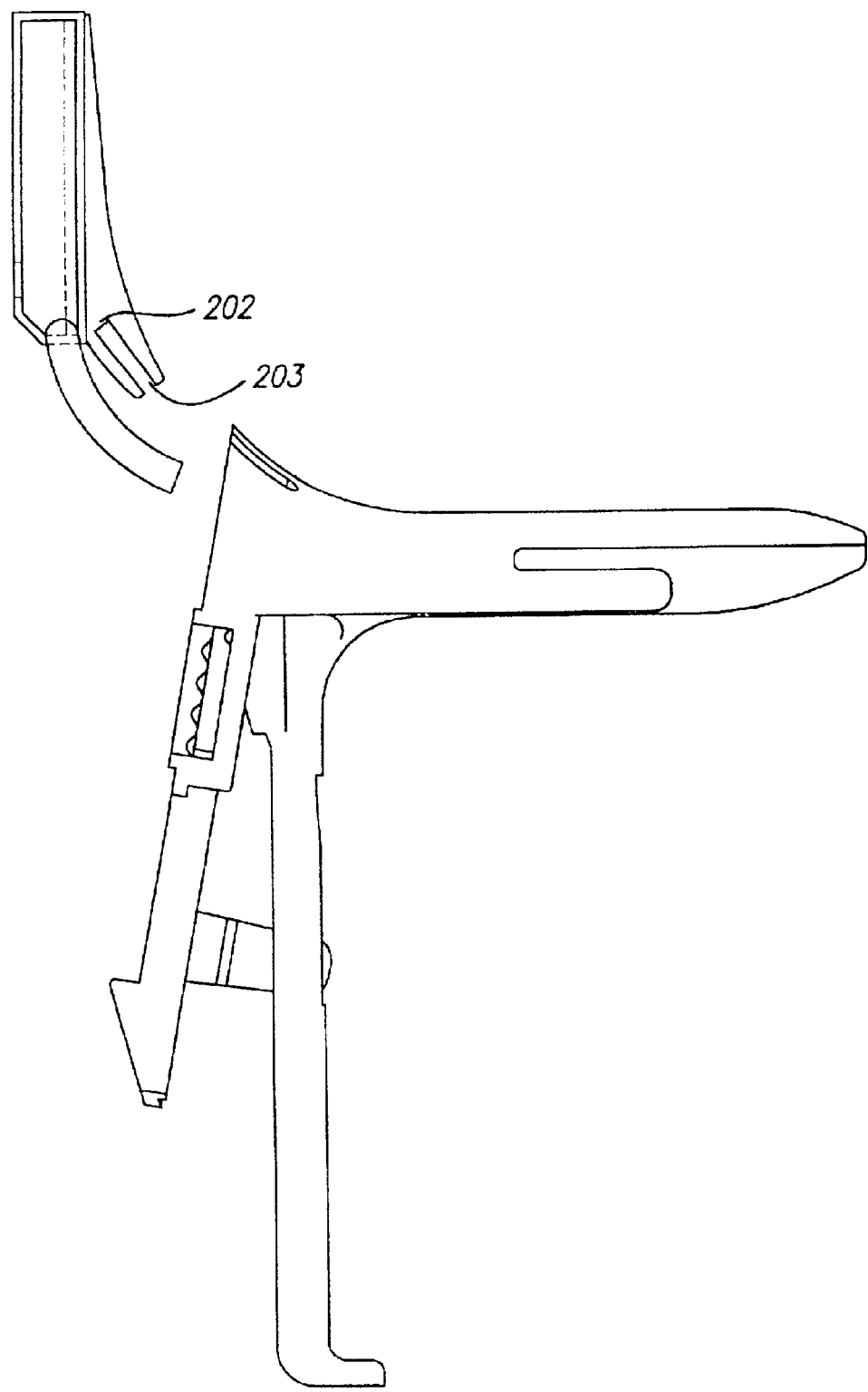
FIG. 17 is a view of both the light-transmitting device with the attachment plate, 202, and the speculum blades (upper and lower).
Figure 18:
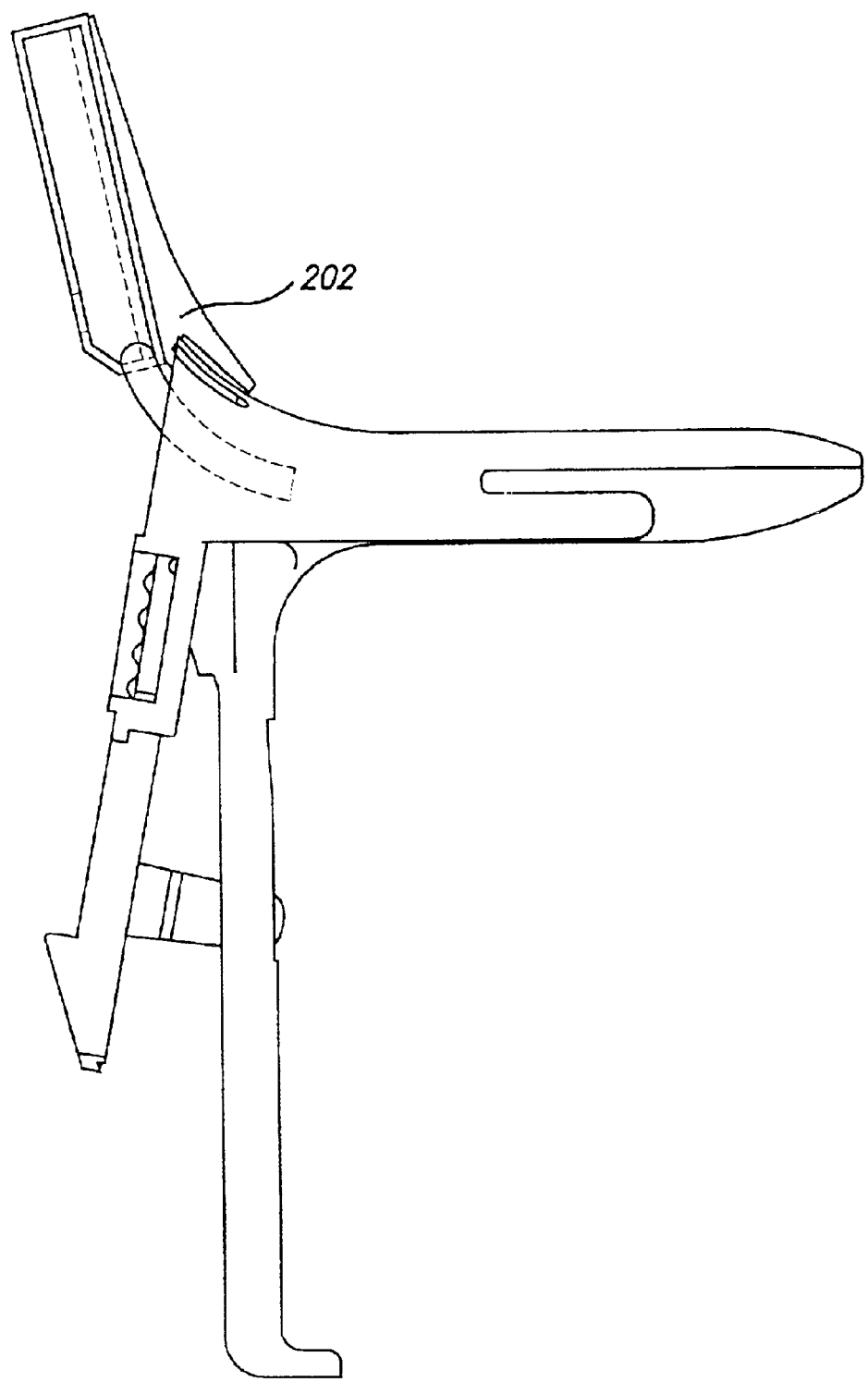
FIG. 18 is a presentation of the light-transmitting device fitting tightly onto the speculum's upper blade by means of the attachment plate.
Figure 19:
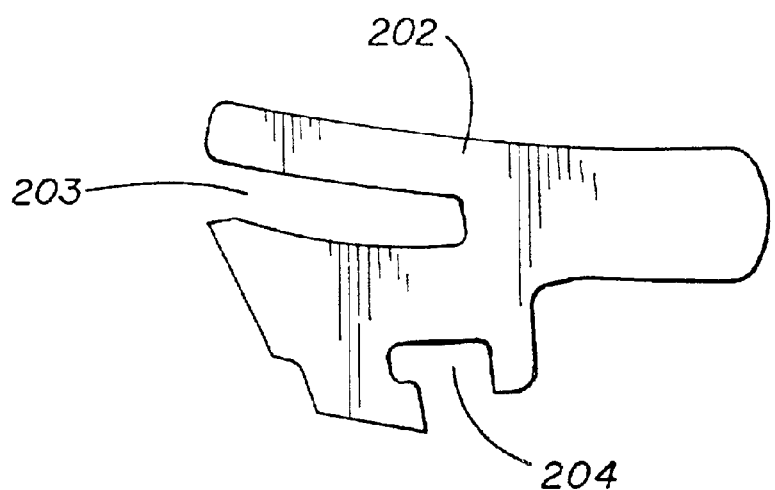
FIG. 19 is a view of the attachment plate to be used in a similar manner as shown in FIG. 18 for receiving an adapted conforming hook placement in the recess, 204.
Figure 20:
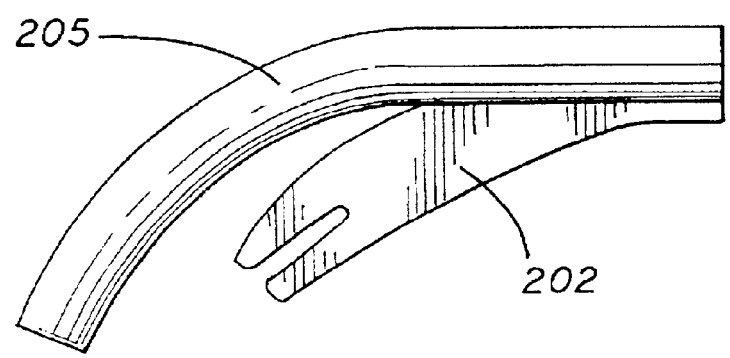
FIG. 20 is a view of the attachment plate and a hollow tube to be used for passing suction tubes and other instruments into the operating field.

There is disclosed in FIGS. 10,12,17,18,19 and 20 an attachment plate 202 and a notch 203 respectively, that allows important functions. First, it permits the cone of light, FIGS. 10 and 12, to be attached to speculums as seen in FIGS. 17 and 18, Secondly, attachments of devices can occur with retractors and other instrumentations where it is advantageous to conduct operations without the use of assistants while holding these devices in place. This attachment plate 202 also allows a receptor recess 204 in FIG. 19 for instruments with hooks to be held in place. A third application for the attachment plate comprises a tube addition 205 permitting tube insertions for suctioning and variable size instrumentations for other operations.

What is claimed is:

1. An attachment apparatus for utilizing an auxiliary device in connection with a speculum, retractor or other surgical or diagnostic instrument, said apparatus comprising:
   (a) a notched element having a notch for engaging said speculum, retractor or other surgical or diagnostic instrument; and
   (b) an elongated tube disposed beneath the notched element,
   wherein the notch extends in a substantially same direction as the elongated tube, and
   wherein the notch comprises two opposing surfaces having an unobstructed gap between, and along a substantial length of, said two opposing surfaces, whereby the notch is capable of engaging a continuous extended surface along said substantial length.

2. An attachment apparatus according to claim 1, wherein the auxiliary device is a light source and the elongated tube is configured for guiding light.

3. An attachment apparatus according to claim 2, further comprising at least one of a light source attached to a proximal end of said elongated tube or means for attaching an external light source to the proximal end of said elongated tube.

4. An attachment apparatus according to claim 2, wherein the elongated tube has a tapered distal end.

5. An attachment apparatus according to claim 1, wherein the elongated tube extends significantly beyond the notched element.

6. An attachment apparatus according to claim 1, wherein the notched element and the elongated tube are comprised of plastic.

7. An attachment apparatus according to claim 1, wherein the notched element is configured as a plate.

8. An attachment apparatus according to claim 1, wherein the notch is configured for engaging a corresponding notch on the speculum, retractor or other surgical or diagnostic instrument.

9. An attachment apparatus according to claim 1, wherein the elongated tube is configured for guiding at least a portion of the auxiliary device.

10. An attachment apparatus according to claim 1, wherein the attachment apparatus is comprised of plastic and is disposable.

11. An attachment apparatus according to claim 1, wherein the elongated tube has a tip comprised of clear plastic.

12. An attachment apparatus according to claim 1, wherein the elongated tube is curved.

13. An attachment apparatus according to claim 12, wherein the elongated tube curves inwardly toward the notch.

14. An attachment apparatus according to claim 11, wherein the notched element and the elongated tube are comprised of metal.

15. An attachment apparatus according to claim 1, wherein the attachment apparatus is comprised of metal.

16. An attachment apparatus according to claim 1, wherein the elongated tube is comprised of a solid clear material and is configured for guiding light.

17. An attachment apparatus according to claim 16, wherein the solid clear material is plastic.

18. An attachment apparatus according to claim 1, wherein the notch engages an upper plate of a speculum.

19. An attachment apparatus for utilizing an auxiliary device in connection with a speculum, retractor or other surgical or diagnostic instrument, said apparatus comprising:
   (a) a notched element having a notch for engaging said speculum, retractor or other surgical or diagnostic instrument, said notched element being disposed toward a forward portion of said attachment apparatus;
   (b) an elongated tube disposed beneath the notched element and extending forwardly beyond the notched element; and
   (c) a connector body that houses at least a portion of the elongated tube.

20. An attachment apparatus according to claim 19, wherein the connector body includes an opening for inserting an illumination source.

21. An attachment apparatus according to claim 20, wherein the connector body includes tracks for stabilizing and centering the illumination source.

22. An attachment apparatus according to claim 21, wherein the illumination source includes a light bulb, and wherein the tracks maintain the illumination source in a position in which the light bulb does not contact any wall of the connector body.

23. An attachment apparatus according to claim 20, wherein the connector body includes an opening near the illumination source for dissipating heat.

24. An attachment apparatus according to claim 20, wherein the connector body is disposed beneath the notched element.

25. An attachment apparatus according to claim 24, wherein the elongated tube curves inwardly toward the notched element as it exits the connector body.

26. An attachment apparatus according to claim 19, wherein the connector body includes an angled tapered front portion for providing dispersion of light.

27. An attachment apparatus for utilizing an auxiliary device in connection with a speculum, retractor or other surgical or diagnostic instrument, said apparatus comprising:
   (a) a notched element having a notch for engaging said speculum, retractor or other surgical or diagnostic instrument; and
   (b) a hook disposed beneath the notched element,
   wherein the notch comprises two opposing surfaces having an unobstructed gap between, and along a substantial length of, said two opposing surfaces, whereby the notch is capable of engaging a continuous extended surface along said substantial length.

28. An attachment apparatus according to claim 27, wherein the notch is configured for engaging a corresponding notch on the speculum, retractor or other surgical or diagnostic instrument.

29. An attachment apparatus according to claim 27, wherein the attachment apparatus is comprised of plastic and is disposable.

* * * * *